United States Patent [19]

Gluchowski

[11] Patent Number: 5,021,416

[45] Date of Patent: Jun. 4, 1991

[54] METHOD FOR USING (2-IMIDAZOLIN-2-YLAMINO) QUINOXALINES TO REDUCE OR MAINTAIN INTRAOCULAR PRESSURE

[75] Inventor: Charles Gluchowski, Mission Viejo, Calif.

[73] Assignee: Allergan, Inc., Irvine, Calif.

[21] Appl. No.: 429,835

[22] Filed: Oct. 31, 1989

[51] Int. Cl.[5] .............................................. A61K 31/50
[52] U.S. Cl. .................................................. 514/249
[58] Field of Search ........................................ 514/249

[56] References Cited

U.S. PATENT DOCUMENTS 3,890,319  6/1975  Danielewicz ........................ 544/284

FOREIGN PATENT DOCUMENTS 2538620  8/1975  Fed. Rep. of Germany .

OTHER PUBLICATIONS

Burke et al. Current Eye Research; Sep. 5 (9): 665-76 (1986).
Mittag. Annals of Ophthalmology 1983; 15(3): 201-202.
Renal Effects of Selective Alpha-1 and Alpha-2 Adrenoceptor Agonists in Conscious, Normotensive Rats; Miklos Gellai & Robert R. Ruffolo, Jr.
Selective Alpha-2 Adrenoceptor Agonists Alter Fluid and Electrolyte Transport in Mammalian Small Intestine; Joseph D. Fondacaro, David Kolpak & Gerald P. McCafferty.
Ocular Effects of a Relatively Selective Alpha-2 Agonist (UK-14, 304-18) in Cats, Rabbits and Monkeys; J. A. Burke and D. E. Potter.
Alpha-2 Adrenergic Modulation of Norepinephrine Secretion in the Perfused Rabbit Iris-Ciliary Body; James E. Jumblatt, John G. H. Liu & Ginnie T. North.
Ocular Effects of Selective Alpha-Adrenergic Agents: A New Drug Paradox? Tom Mittag, Ph.D.
Mechanism of Alpha-2-Adrenoceptor Agonist-Induced Diuresis Miklos Gellai & Richard M. Edwards.
Clonidine and Some Bridge Analogues; Cardiovascular Effects and Nuclear Magnetic Resonance Data (H/C); Pieter B.M.W.M. Timmermans & Pieter A. van Zwieten.
Alpha-2-Adrenergic Receptors Accelerate Na/H Exchange in Neuroblastoma X Glioma Cells* Lori L. Isom; E. J. Cragoe, Jr.; and Lee E. Limbird.
Clonidine: New Research in Psychotropic Drug Pharmacology; Stuart Fielding, Harbans Lal.
Clonidine and Related Compounds; Bevyn Jarrott.
Alpha-2 Adrenergic Agonists: A Newer Class of Antidiarrheal Drug Gastroenterology 1986:91:769-75.

*Primary Examiner*—Stanley J. Friedman
*Assistant Examiner*—Zohreh A. Fay
*Attorney, Agent, or Firm*—Gordon L. Peterson; Frank J. Uxa, Jr.

[57] ABSTRACT

Certain (2-imidazolin-2-ylamino) quinoxalines are disclosed. Such quinoxalines reduce or maintain intraocular pressure when administered directly to the eye of a mammal.

28 Claims, No Drawings

METHOD FOR USING (2-IMIDAZOLIN-2-YLAMINO) QUINOXALINES TO REDUCE OR MAINTAIN INTRAOCULAR PRESSURE

BACKGROUND OF THE INVENTION

The present invention relates to a method for reducing or maintaining intraocular pressure. More particularly, it relates to a method for reducing or maintaining intraocular pressure involving the administration of an effective amount of a (2-imidazolin-2-ylamino) quinoxaline and/or a salt thereof, e.g., in an ophthalmically acceptable carrier.

The method of the present invention is particularly useful for the management of glaucoma, a disease of the eye characterized by increased intraocular pressure. On the basis of its etiology, glaucoma has been classified as primary or secondary. For example, primary glaucoma in adults may be either chronic open-angle or acute or chronic angle-closure. Secondary glaucoma results from pre-existing ocular diseases such as uveitis, intraocular tumor or an enlarged cataract.

The underlying causes of primary glaucoma are not yet well known. The increased intraocular pressure is due to obstruction of aqueous humor outflow. In chronic open-angle glaucoma, the anterior chamber and its anatomic structures appear normal, but drainage of the aqueous humor is impeded. In acute and chronic angle-closure glaucoma, the anterior chamber is shallow, the filtration angle is narrowed and the iris may obstruct the trabecular meshwork at the entrance to the canal of Schlemm. Dilation of the pupil may push the root of the iris forward against the angle or may produce pupillary block and thus precipitate an acute attack. Eyes with narrow anterior chamber angles are predisposed to acute angle-closure glaucoma attacks of varying degrees of severity.

Secondary glaucoma is caused by any interference with the flow of aqueous humor from the posterior chamber into the anterior chamber and, subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptomatic for years before progressing to rapid loss of vision. In cases where surgery is not indicated, topical beta-adrenoceptor antagonists have traditionally been the drugs of choice for treating glaucoma.

Various quinoxaline derivatives have been suggested as therapeutic agents. For example, Danielewicz, et al U.S. Pat. No. 3,890,319 discloses compounds as regulators of the cardiovascular system which have the following formula:

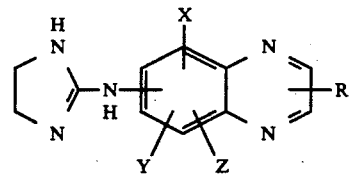

where the 2-imidazolin-2-ylamino group may be in any of the 5-, 6-, 7- or 8- position of the quinoxaline nucleus; X, Y and Z may be in any of the remaining 5-, 6-, 7- or 8- positions and may be selected from hydrogen, halogen, lower alkyl, lower alkoxy or trifluoromethyl; and R is an optional substituent in either tho 2- or 3- position of the quinoxaline nucleus and may be hydrogen, lower alkyl or lower alkoxy. There is no suggestion in the Daniolewicz, et al patent that such compounds are useful in reducing or maintaining intraocular pressure.

In "Ocular effects of a relatively selective alpha 2 agonist (UK-14, 304-18) in cats, rabbits and monkeys", by J.A. Burke et al, Current Eye Research, Vol. 5, Nov. 9, 1986, the quinoxaline derivative

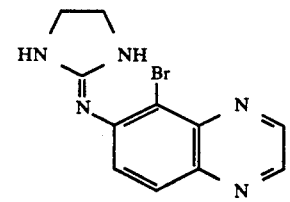

was shown to be effective to reduce intraocular pressure in rabbits, cats and monkeys. No other quinoxaline derivatives were suggested as being useful to reduce intraocular pressure.

SUMMARY OF THE INVENTION

A new method for reducing or maintaining the intraocular pressure in a mammalian eye has been discovered. This method comprises administering directly to a mammalian eye an effective amount of one or more of certain (2-imidazoline-2-ylamino) quinoxalines (as defined herein), salts thereof and mixtures thereof. This new method is particularly effective in the treatment or management of mammalian, e.g., human, eyes affected with glaucoma.

DETAILED DESCRIPTION OF THE INVENTION

The (2-imidazolin-2-ylamino) quinoxalines useful in the present invention are those which when administered directly into a mammalian eye are effective to reduce or maintain, preferably reduce, the intraocular pressure in the mammalian eye. Two types of quinoxaline derivatives are included within the scope of the present invention.

One type of quinoxaline derivative useful in the present invention are those quinoxaline derivatives having the formula

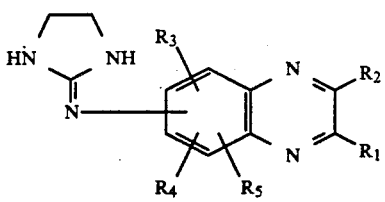

, pharmaceutically acceptable acid addition salts thereof and mixtures thereof. $R_1$ is H, and $R_2$ is selected from the group consisting of alkyl radicals containing 1 to 4 carbon atoms and alkoxy radicals containing 1 to 4 carbon atoms. $R_2$ is preferably a methyl radical. The 2-imidazolin-2-ylamino group may be in any of the 5-, 6-, 7- or 8- positions, preferably in the 6- position, of the quinoxaline nucleus. $R_3$, $R_4$ and $R_5$ each is located in one of the remaining 5-, 6-, 7- or 8-positions of the quinoxaline nucleus and is independently selected from the group consisting of Cl, Br, H and alkyl radicals containing 1 to 3 carbon atoms. $R_3$ is preferably in the 5-position of the quinoxaline nucleus, and $R_4$ and $R_5$ are preferably both H. In a particularly useful embodiment $R_3$ is Br.

Another type of quinoxaline derivative useful in the present invention are those quinoxaline derivatives having the formula

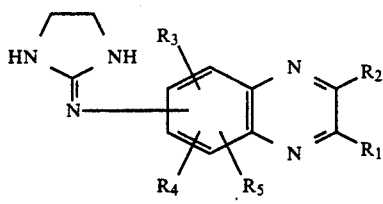

, pharmaceutically acceptable acid addition salts thereof and mixtures thereof. In this formula, $R_1$ and $R_2$ are independently selected from the group consisting of H, alkyl radicals containing 1 to 4 carbon atoms and alkoxy radicals containing 1 to 4 carbon atoms Preferably, both $R_1$ and $R_2$ are H. The 2-imidazolin-2-ylamino group may be in any of the 6-, 7- or 8- positions, preferably in the 6- position, of the quinoxazoline nucleus. $R_3$ is selected from the group consisting of H and alkyl radicals containing 1 to 3 carbon atoms. Preferably, $R_3$ is selected from H and methyl. $R_4$ and $R_5$ each is located in one of the remaining 6-, 7-, or 8-positions of the quinoxaline nucleus and is selected from Cl, Br, H and alkyl radicals containing 1 to 3 carbon atoms. Preferably both $R_4$ and $R_5$ are H.

All stereoisomers, tautomers and mixtures thereof which comply with the constraints of one or more of the presently useful compounds are included within the scope of the present invention.

The present method is particularly effective in a strategy for the treatment or management of glaucoma, whether primary or secondary glaucoma. In this embodiment, one or more of the presently useful compounds are preferably administered directly to a mammalian eye affected with glaucoma to effectively reduce or maintain, preferably control, the intraocular pressure in the glaucoma-affected eye.

The presently useful compounds are often administered to the eye in the form of a mixture with an ophthalmically acceptable carrier. Any suitable, e.g., conventional, ophthalmically acceptable carrier may be employed. Such a carrier is ophthalmically acceptable if it has substantially no long term or permanent detrimental effect on the eye to which it is administered. Examples of ophthalmically acceptable carriers include water, in particular distilled water, saline and the like aqueous media. The presently useful compounds are preferably administered to the eye as a liquid mixture with the carrier. The compounds are more preferably soluble in the carrier so that the compounds are administered to the eye in the form of a solution.

When an ophthalmically acceptable carrier is employed, it is preferred that the mixture contain one or more of the presently useful compounds in an amount in the range of about 0.0001% to about 1%, more preferably about 0.05% to about 0.5%, W/V.

Any method of administering drugs directly to a mammalian eye may be employed to provide the presently useful compound or compounds to the eye to be treated. By the term "administering directly" is meant to exclude those general systemic drug administration modes, e.g., injection directly into the patients blood vessels, oral administration and the like, which result in the compound or compounds being systemically available. The primary effect on the mammal resulting from the direct administering of the presently useful compound or compounds to the mammal's eye is preferably a reduction in intraocular pressure. More preferably, the presently useful compound or compounds are applied topically to the eye or are injected directly into the eye. Particularly useful results are obtained when the compound or compounds are applied topically to the eye.

Topical ophthalmic preparations, for example ocular drops, gels or creams, are preferred because of ease of application, ease of dose delivery, and fewer systemic side effects, such as cardiovascular hypotension. An exemplary topical ophthalmic formulation is shown below in Table I. The abbreviation q.s. means a quantity sufficient to effect the result or to make volume.

TABLE I

| Ingredient | Amount(% W/V) |
| --- | --- |
| (2-imidazolin-2-ylamino) quinoxaline | about 0.0001 to about 1.0 |
| Preservative | 0–0.10 |
| Vehicle | 0–40 |
| Tonicity Adjustor | 1–10 |
| Buffer | 0.01–10 |
| pH Adjustor | q.s. pH 4.5–7.5 |
| antioxidant | as needed |
| Purified Water | as needed to make 100% |

Various preservatives may be used in the ophthalmic preparation described in Table I above. Preferred preservatives include, but are not limited to, benzalkonium chloride, chlorobutanol, thimerosal, phenylmercuric acetate, and phenylmercuric nitrate. Likewise, various preferred vehicles may be used in such ophthalmic preparation. These vehicles include, but are not limited to, polyvinyl alcohol, povidone, hydroxypropyl methyl cellulose, poloxamers, carboxymethyl cellulose, hydroxyethyl cellulose, and purified water.

Tonicity adjustors may be added as needed or convenient. They include, but are not limited to, salts, particularly sodium chloride, potassium chloride, mannitol, and glycerin, or any other suitable ophthalmically acceptable tonicity adjustor.

Various buffers and means for adjusting pH may be used so long as the resulting preparation is ophthalmically acceptable. Accordingly, buffers include but are not limited to, acetate buffers, citrate buffers, phosphate buffers, and borate buffers. Acids or bases may be used to adjust the pH of these formulations as needed.

In a similar vein, ophthalmically acceptable antioxidants include, but are not limited to, sodium metabisulfite, sodium thiosulfate, acetylcysteine, butylated hydroxyanisole, and butylated hydroxytoluene.

Other excipient components which may be included in the exemplary ophthalmic preparation described in Table I are chelating agents which may be added as needed. The preferred chelating agent is edetate disodium, although other chelating agents may also be used in place of or in conjunction with it.

Pharmaceutically acceptable acid addition salts of the presently useful compounds are those formed from acids which form non-toxic addition salts containing pharmaceutically acceptable anions, such as the hydrochloride, hydrobromide, hydroiodide, sulphate or bisulfate, phosphate or acid phosphate, acetate, maleate, fumarate, oxalate, lactate, tartrate, citrate, gluconate, saccharate and p-toluene sulphonate salts.

The presently useful compounds may be prepared in accordance with the procedures described in Danielewicz, et al U.S. Pat. No. 3,890,319 for the production of the quinoxaline derivatives therein. This patent is hereby incorporated in its entirety by reference herein.

Briefly, the presently useful 2-imidazolin-2-ylamino quinoxaline derivatives may be prepared by (1) reaction of the appropriate amino-quinoxaline with thiophosgene to form the corresponding isothiocyanate; and (2) reacting this isothiocyanate with excess ethylene diamine to form the corresponding beta-aminoethyl-thioureidoquinoxaline, which is then cyclized to the corresponding derivative. Alternately, such derivatives can be prepared by (1) reacting the corresponding aminoquinoxaline with benzoyl isothiocyanate to form the corresponding N-benzoyl thioureido compound, followed by hydrolysis to the thioureido compound, or reaction of the aminoquinoxaline with ammonium thiocyanate to form the thioureido compound directly; (2) methylation to form the S-methyl derivative of the thioureido compound; and (3) reaction with ethylene diamine to form the derivative.

For derivatives in which the $R_3$ group is to be alkyl, the corresponding bromo derivative can be produced and then subjected to an alkylation reaction in which the bromo group is replaced by the desired alkyl group. This alkylation reaction is conveniently conducted using an alkylation agent, such as an alkyl metallic component, e.g., alkyl stannane, in the presence of a platinum group metal-containing catalyst. For example, if it is desired to substitute a methyl group for the bromo group, the bromo derivative is contacted with tetramethyl tin in the presence of a palladium-containing catalyst, e.g. $(Ph_3 P)_2 PdCl_2$, at conditions to effect the desired alkylation or substitution.

The following non-limiting examples illustrate certain aspects of the present invention.

EXAMPLE 1

Preparation of 6-(2-imidazolin-2-ylamino) quinoxaline 1,2,4-Triaminobenzene dihydrochloride To a suspension of 4-nitrophenylenediamine (Aldrich, 10 g, 65.3 mmol) in absolute ethanol (240 ml) was added 600 mg of 10% by weight palladium on charcoal catalyst. The container including the suspension was evacuated and filled with hydrogen three times and the suspension was hydrogenated at 18 psi until hydrogen uptake ceased. The reaction was slightly exothermic and one refill of hydrogen was required. The resulting light yellow solution, which darkens rapidly on contact with air, was filtered and concentrated to about 150 ml. Concentrated hydrochloric acid (12 ml) was added and the solid formed was filtered off. After drying in vacuo overnight, 12 g (a yield of 93%) of purple solid was obtained, m.p. 224–5° C. Using various analytical procedures, this solid was determined to be 1,2,4-triaminobenzene dihydrochloride.

6-Aminoquinoxaline

Glyoxal sodium bisulfite adduct (Aldrich, 14.3 g, 50 mmol) was added in small portions to a solution of 1,2,4-triaminobenzene dihydrochloride (9.8 g, 50 mmol) in 200 ml of 10% by weight sodium carbonate in water. The reaction mixture was heated to 100° C. for two hours and then cooled to 0° C. The crystals formed were filtered off and dried in vacuo to give a crude yield of 7.06 g (a yield of 97%) of brown crystals. Recrystallization from benzene gave 6.32 g (a yield of 87%) yellow crystals, m.p. 157°–8° C. Using various analytical procedures, these yellow crystals were determined to be 6-aminoquinoxaline.

6-(2-imidazolin-2-ylamino) quinoxaline

6-Aminoquinoxaline (1.00 g, 7.5 mmol) was suspended in 15 ml of water and thiophosgene (0.64 ml, 8.4 mmol) was added in small portions with vigorous stirring. The starting material dissolved and after 2 hours the red color of the solution was discharged. The solid formed was removed by vacuum filtration and washed with water. The crude isothiocyanate thus obtained was used without further purification. A solution of the isothiocyanate in benzene (70 ml) was contacted with ethylenediamine (Aldrich, 2.71 g, 45 mmol) in 10 ml of benzene at 25° C. for 30 minutes. After stirring for an additional 30 minutes, the supernatant was poured off. The crude thiourea thus obtained was washed three (3) times with 10 ml dry ether and used directly for the next step. The crude product was dissolved in 30 ml of dry methanol and the dark green solution was heated at reflux for 15 hours until hydrogen sulfide gas was no longer evolved. The mixture was cooled to room temperature and concentrated in vacuo. The resulting dark green solid was chromatographed ($SiO_2$, 90/10 $CHCl_3/CH_3OH$ saturated with $NH_3$ (g)) to yield a dark green solid which was recrystallized from $CH_3OH$ to yield 1.11 g of the title compound as a light green crystalline solid, mp 232°–234° C. The yield was 70%. The compound was characterized by $^1H$ and $^{13}CNMR$, IR and mass spectral analysis.

EXAMPLE 2

Preparation of 5-methyl-6-(2-imidazolin-2-ylamino) quinoxaline

6-Amino-5-bromoquinoxaline hydrobromide

6-Aminoquinoxaline (2.08 g, 14.4 mmol) was dissolved in 11.5 ml glacial acetic acid. The solution was cooled in water while a solution of bromine (0.74 ml, 2.3 g, 14.4 mmol) in 1.5 ml glacial acetic acid was added slowly over 15 min. After stirring for an additional 30 min, the orange red solid formed was filtered off and washed thoroughly with dry ether. The solid was dried in vacuo overnight to yield 4.44 g crude product (a yield of 100%). The compound, 6-amino-5- bromoquinoxaline hydrobromide, had no definite melting point. A phase change (from fine powder to red crystals) was noticed at about 220° C. Decomposition was observed at about 245° C. It was used directly for the next step.

6-Amino-5-Bromoquinoxaline

The crude 6-amino-5-bromoquinoxaline from above was dissolved in water and saturated sodium bisulfite solution was added until the resulting solution tested negative with starch-iodide paper. The solution was then basified with 2N sodium hydroxide and extracted thoroughly with ethyl acetate. The organic extract was dried over magnesium sulfate and concentrated under reduced pressure to give the free base. The crude product was recrystallized from boiling benzene to give yellow crystals, m.p. 155°–6° C. Using various analytical procedures, the yellow crystals were determined to be 6-amino-5-bromoquinoxaline. The yield was 82%.

5-Bromo-6-isothiocyanatoquinoxaline

The crude hydrobromide product previously noted (4.27 g, 14.0 mmol) Was dissolved in 60 ml of water and thiophosgene (Aldrich, 1.28 ml, 16.8 mmol) was added in small portions with vigorous stirring. After 2 hours, the red color of the solution was discharged. The solid formed was filtered off and washed thoroughly with water. After drying in vacuo at 25° C., 3.38 g (a yield of 90%) of brick red crystals was obtained, m.p. 157°–8° C. A portion of this material was further purified by column chromatography to give white crystals, m.p. 157°–8° C. Using various analytical procedures, these crystals were determined to be 5-bromo-6-isothiocyanatoquinoxaline.

5-Bromo-6(-N -(2-aminoethyl)thioureido)quinoxaline

A solution of the isothiocyanate (3.25 g, 12.2 mmol) in 145 ml benzene was added to a solution of ethylenediamine (Aldrich, 5.43 g, 90.0 mmol) in 18 ml benzene at 25° C. over 2 hours. After stirring for a further 30 min., the supernatant was poured off. The oil which remained was washed by swirling with dry ether three times and used directly for the next step.

A portion of this product was further purified by column chromatography (SiO2, CHCl3) for characterization. A white solid was recovered which decomposed at 175° C. with gas evolution (puffing). This white solid was determined to be 5-bromo-6(-N-2-(aminoethyl)thioureido) quinoxaline.

5-Bromo-6-(2-imidazolin-2-ylamino)quinoxaline

The crude product from above was dissolved in 100 ml dry methanol and the brown solution was refluxed for 19 hours until hydrogen sulfide gas was no longer evolved. The mixture was cooled to room temperature and concentrated to about 50 ml. The yellow solid was filtered off and dried in vacuo; weight 2.52 g (a yield of 70%), mp 242°–4° C.

As the crude product was insoluble in most common organic solvents, initial purification was achieved by an acid-base extraction procedure. 23 g of the crude product was dissolved in 100 ml 0.5N hydrochloric acid. The turbid yellow solution was filtered to give a clear orange yellow solution which was extracted twice with ethyl acetate (2×10 ml). The aqueous phase was cooled to 0° C. and basified with 6N sodium hydroxide, keeping the temperature of the solution below 15° C. at all times. The yellow solid which precipitated was filtered off and washed thoroughly with water until the washings were neutral to pH paper. The solid was dried overnight in vacuo to give 1.97 g yellow solid, m.p. 249°–50° C. The recovery was about 88%.

Further purification was achieved by recrystallization as described below. The partially purified product from above was dissolved in N, N-dimethylformamide (about 17 ml/g) at 100° C. with vigorous stirring. The solution was filtered hot and set aside to cool overnight. The bright yellow crystals were collected by filtration, m.p. 252°–3 C. Recovery was from 65-77%. Using various analytical procedures, the bright yellow solid was determined to be 5-bromo-6-(2-imidazolin-2-ylamino) quinoxaline.

0 5-Methyl-6-(2-imidazolin-2-ylamino)quinoxaline

A sealable reaction tube was charged with 5-bromo-6-(2-imidazolin-2-ylamino) quinoxaline (104 mg., 0.36 mmol), tetramethyl tin (214 mg., 1.2 mmol) and (Ph3P)2PdCl2 (10 mg) and dry dimethylformamide (2 ml) in a reaction tube. The reaction mixture was purged with dry nitrogen gas. The tube was sealed and heated to 145° C. for 6 hours. The reaction mixture was cooled to room temperature and the solvent removed in vacuo. The dark brown residue was chromatographed (SiO2; 5/1 CHCl3/CH3OH saturated with NH3 (g)) to yield 46.5 mg (53%) of the title compound as a light yellow solid. An analytical sample was prepared by recrystallization from CHCl3/CH3OH and had a melting point of 183°–186° C. The compound was characterized by $^1$H and $^{13}$CNMR, IR and mass spectral analysis.

EXAMPLE 3

Preparation of 2-Methyl-5-bromo-6-(2-imidazolin-2-ylamino)-quinoxaline

2-Methyl-6-nitroquinoxaline

A solution of pyruvic aldehyde (Aldrich, 40% solution in H2O, 11.8 g, 65.3 mmol) was added dropwise to a solution of 4-nitro-1,2-phenylenediamine (Aldrich, 10 g, 65.3 mmol) in 150 ml of H2O. The reaction mixture was heated to 80° C. for four hours. The reaction was cooled to room temperature, diluted with water and extracted with CHCl3. The organic extracts were dried over MgSO4 and evaporated to yield 10.7 g (a yield of 87%) of as a brick red solid. Using various analytical procedures, this solid was determined to be 2-methyl-6-nitroquinoxaline.

b 2-Methyl-6-Aminoquinoxaline

A thick-walled Parr hydrogenation flask was charged with 2-methyl-6-nitroquinoxaline (10.0 g, 52.9 mmol) and CH3OH (200 ml). The flask was flushed with a stream of nitrogen and 10% by weight palladium on charcoal (500 mg) was added. The flask was pressurized with hydrogen to 50 psi and maintained at this pressure for three (3) hours. The reaction mixture was filtered and washed through silicon dioxide and concentrated in vacuo to yield a tan solid. The crude material was chromatographed (SiO2;95/5 CHCl3/CH3OH saturated with NH3(g)) and recrystallized from benzene to yield 7.4 g (a yield of 88%) of a tan solid. Using various analytical procedures, this tan solid was determined to be 2-methyl-6-aminoquinoxaline.

2-Methyl-5-bromo-6-(2-imidazolin-2-ylamino) quinoxaline

By a series of reaction steps analogous to the reaction steps described above in Example 2 to produce 5-bromo-6-(2-imidazolin-2-ylamino) quinoxaline, the title compound (mp. 260° C.) was prepared starting with 2-methyl-6-aminoquinoxaline in place of 6-aminoquinoxaline.

EXAMPLE 4

Preparation of 3-Methyl-5-bromo-6-(2-imidazolin-2 ylamino)-quinoxaline

3-Methyl-6-aminoquinoxaline

Pyruvic aldehyde (Aldrich, 892 mg, 4.95 mmol, 40% solution $H_2O$) was added dropwise to a stirred solution of 1, 2, 4-triaminobenzene hydrochloride (1.0 g, 4.95 mmol) dissolved in 10% aqueous $Na_2CO_3$ (15 ml). The mixture was heated at 100° C. for two hours before cooling to room temperature. The mixture was extracted with $CHCl_3$. The combined organic extracts were dried over $MgSO_4$ and concentrated in vacuo to yield a brown solid. The crude product was chromatographed ($SiO_2$, 95/5 $CHCl_3/CH_3OH$ saturated with $NH_3$ (g)) to yield 616 mg (a yield of 75%) of a yellow crystalline solid. An analytical sample was prepared by recrystallization from benzene, mp 170°-173° C. Using various analytical procedures, the solid was determined to be 3-methyl-6-aminoquinoxaline.

3-Methyl-5-bromo-6-(2-imidazolin-2-ylamino)-quinoxaline

By a series of reaction steps analogous to the reaction steps described above in Example 2 to produce 5-bromo-6-(2 imidazolin-2-ylamino) quinoxaline, the title compound (mp>260° C.) was prepared starting with 3-methyl-6-aminoquinoxaline in place of 6-aminoquinoxaline.

EXAMPLE 5

Preparation of 2,3-dimethyl-5-bromo-6-(2-imidazoline-2-ylamino, quinoxaline.

2,3-Dimethyl-6-aminoquinoxaline 2,3-butanedione (7.03 g, 81.7 mmol) was added to a solution of 1,2,4-triaminobenzene hydrochloride (16.5 g, 81.7 mmol) in aqueous 10% $Na_2CO_3$ (200 ml). The reaction mixture was stirred at room temperature for 15 minutes during which time a yellow precipitate formed. The reaction mixture was stirred for an additional 30 minutes before collecting the solid by vacuum filtration. The solid was washed with water, dried in vacuo and chromatographed ($SiO_2$, ethylacetate) to yield 11.7 g (86%) of a tan solid, mp 185°-186° C. Using various analytical procedures, this solid was determined to be 2,3-dimethyl-6-aminoquinoxaline.

2,3-dimethyl-5-bromo-6-(2-imidazolin-2-ylamino)-quinoxaline

By a series of reaction steps analogous to the reaction steps described above in Example 2 to produce 5-bromo-6-(2-imidazolin-2-ylamino) quinoxaline, the title compound (mp 252°-254° C.) was prepared starting with 2,3-dimethyl-6-aminoquinoxaline in place of 6-aminoquinoxaline.

EXAMPLE 6 to 10

The five (5) quinoxaline derivatives produced in accordance with Examples 1 to 5 were tested to determine what effect, if any, these materials have on intraocular pressure.

Each of these materials was dissolved in distilled water at a concentration of 0.1% (W/V). Each of these solutions was administered topically and unilaterally to one eye of a drug-naive, unanesthetized New Zealand white rabbit in a single 50 micro liter drop. The contralateral eye received an equal volume of saline prior to determining the intraocular pressure after the mixture was administered. Also, approximately 10 micro liters of 0.5% (W/V) proparacaine (topical anesthetic) was applied to the corneas of each of the rabbits before determining intraocular pressure. As a control test, six (6) other drug-naive, unanesthetized New Zealand white rabbits were treated and tested as described above except that no quinoxaline derivative was included in the solutions administered to the eyes.

The intraocular pressure was determined in both eyes of each rabbit before and after the solutions were administered. Such intraocular pressure determinations were made in the conventional manner using conventional equipment.

Results of these IOP determinations were as follows:

| Active Material | Difference In Intraocular Pressure, percent | | |
|---|---|---|---|
| | Initial Effect On Treated Eye | Maximum Effect On Treated Eye | Maximum Effect On Untreated Eye |
| Example | | | |
| 6. 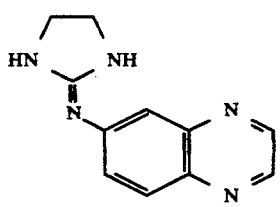 | 11.8 ± 1.8 | −18.6 ± 3.2 | −9.6 ± 1.4 |
| 7. 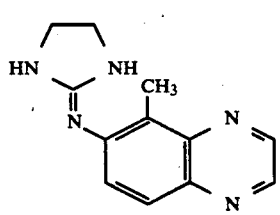 | N.S. | −21.9 ± 3.6 | −5.4 ± 2.0 |

| | Difference In Intraocular Pressure, percent | | |
|---|---|---|---|
| Active Material | Initial Effect On Treated Eye | Maximum Effect On Treated Eye | Maximum Effect On Untreated Eye |
| 8. ![structure 8] | N.S. | N.S. | N.S. |
| 9. ![structure 9] | N.S. | $-22.5 \pm 1.8$ | N.S. |
| 10. ![structure 10] | N.S. | N.S. | N.S. |
| Control | N.S. | N.S. | N.S. |

N.S. means that the effect was not statistically significant.

These results indicated that the quinoxaline derivatives used in Examples 6, 7 and 9 are effective to reduce intraocular pressure in the treated rabbit eye, i.e., the eye to which the active material was directly administered. The quinoxaline derivative used in Example 6 had an initial effect in the treated eye of raising the intraocular pressure. These results are particularly surprising in view of the insignificant effect on intraocular pressure of the materials used in Examples 8 and 10, which materials are structurally closely related to the other materials tested.

While this invention has been described with respect to various specific examples and embodiments, it is to be understood that the invention is not limited thereto and that it can be variously practiced within the scope of the following claims.

What is claimed is:

1. A method for reducing or maintaining the intraocular pressure in a mammalian eye comprising administering directly to a mammalian eye an amount effective to reduce or maintain the intraocular pressure in the mammalian eye of a compound selected from the group consisting of those having the formula

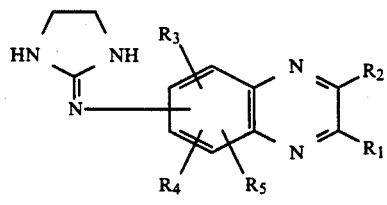

, and pharmaceutically acceptable acid addition salts thereof and mixtures thereof, wherein $R_1$ is H, $R_2$ is selected from the group consisting of alkyl radicals containing 1 to 4 carbon atoms and alkoxy radicals containing 1 to 4 carbon atoms, the 2-imidazolin-2-ylamino group may be in any of the 5-, 6-, 7-or 8- positions of the quinoxaline nucleus, and $R_3$, $R_4$ and $R_5$ each is located in one of the remaining 5-, 6-, 7- or 8-positions of the quinoxaline nucleus and is independently selected from the group consisting of Cl, Br, H and alkyl radicals containing 1 to 3 carbon atoms.

2. The method of claim 1 wherein said compound is administered directly to the mammalian eye in an amount effective to reduce the intraocular pressure in the mammalian eye.

3. The method of claim 1 wherein said administering includes at least one of applying said compound topically to the mammalian eye and injecting said compound directly into the mammalian eye.

4. The method of claim 1 wherein said compound is administered in the form of a mixture with an ophthalmically acceptable carrier.

5. The method of claim 4 wherein said mixture is a liquid at the time of said administering.

6. The method of claim 4 wherein said compound is present in said mixture in an amount in the range of about 0.0001% to about 1% (W/V).

7. The method of claim 1 wherein the mammalian eye is affected with glaucoma.

8. The method of claim 1 wherein the 2-imidazolin-2-ylamino group is in the 6- position of the quinoxaline nucleus, $R_3$ is in the 5- position of the quinoxaline nucleus and is selected from the group consisting of Cl, Br and alkyl radicals containing 1 to 3 atoms, and $R_4$ and $R_5$ are both H.

9. The method of claim 1 wherein $R_2$ is a methyl radical.

10. The method of claim 8 wherein $R_2$ is a methyl radical.

11. The method of claim 8 wherein $R_3$ is Br.

12. The method of claim 10 wherein $R_3$ is Br.

13. The method of claim 1 wherein said formula is:

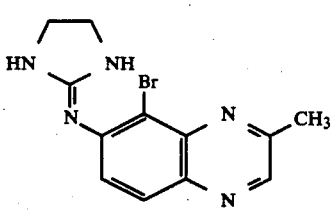

14. A method for reducing or maintaining the intraocular pressure in a mammalian eye comprising administering directly to a mammalian eye an amount effective to reduce or maintain the intraocular pressure in the mammalian eye of a compound selected from the group consisting of those having the formula

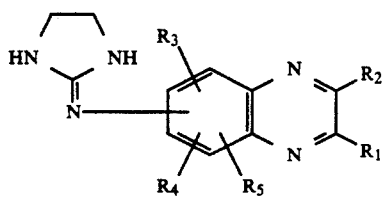

,and pharmaceutically acceptable acid addition salts thereof and mixtures thereof, wherein $R_1$ and $R_2$ are independently selected from the group consisting of H, alkyl radicals containing 1 to 4 carbon atoms and alkoxy radicals containing 1 to 4 carbon atoms, the 2-imidazolin-2-ylamino group may be in any of the 6-, 7- or 8-positions of the quinoxaline nucleus, $R_3$ is selected from the group consisting of H and alky radicals containing 1 to 3 carbon atoms, and $R_4$ and $R_5$ each is located in one of the remaining 6-, 7- or 8- positions of the quinoxaline nucleus and is selected from the group consisting of Cl, Br, H and alkyl radicals containing 1 to 3 carbon atoms.

15. The method of claim 14 wherein said compound is administered directly to the mammalian eye in an amount effective to reduce the intraocular pressure in the mammalian eye.

16. The method of claim 14 wherein said administering includes at least one of applying said compound topically to the mammalian eye and injecting said compound directly into the mammalian eye.

17. The method of claim 14 wherein said compound is administered in the form of a mixture with an ophthalmically acceptable carrier.

18. The method of claim 17 wherein said mixture is a liquid at the time of said administering.

19. The method of claim 17 wherein said compound is present in said mixture in an amount in the range of about 0.0001% to about 1% (W/V).

20. The method of claim 14 wherein the mammalian eye is affected with glaucoma.

21. The method of claim 14 wherein the 2-imidazolin-2-ylamino group is in the 6- position of the quinoxaline nucleus, and $R_4$ and $R_5$ are both H.

22. The method of claim 14 wherein both $R_1$ and $R_2$ are H.

23. The method of claim 21 wherein both $R_1$ and $R_2$ are H.

24. The method of claim 14 wherein $R_3$ is selected from the group consisting of H and methyl radical.

25. The method of claim 21 wherein $R_3$ is selected from the group consisting of H and methyl radical.

26. The method of claim 23 wherein $R_3$ is selected from the group consisting of H and methyl radical.

27. The method of claim 14 wherein said formula is:

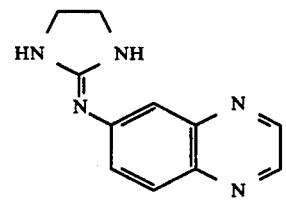

28. The method of claim 14 wherein said formula is:

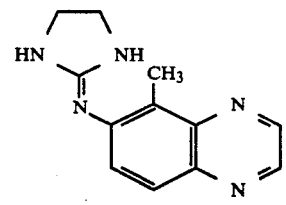

* * * * *

UNITED STATES PATENT AND TRADEMARK OFFICE
CERTIFICATE OF CORRECTION

PATENT NO. : 5,021,416
DATED : June 4, 1991
INVENTOR(S) : Charles Gluchowski It is certified that error appears in the above-identified patent and that said Letters Patent is hereby corrected as shown below:

Col. 2, line 16 change "tho" to -- the --.
Col. 2, line 24 change "Nov." to -- No. --.

Col. 3, line 42 between "atoms" and "Preferably" insert a period.

Col. 7, line 21 change "Was" to -- was --.

Col. 8, line 7 change "252°-3" to -- 252°-3° --.

Col. 8, line 11, delete "0".

Col. 8, line 45 delete "b".

Col. 9, line 32 after "ylamino" delete the comma and insert -- ) --.

Col. 10, line 15 change "Example" to -- Examples --.

Col. 13, line 41 change "alky" to -- alkyl --.

Signed and Sealed this

Ninth Day of March, 1993

Attest:

STEPHEN G. KUNIN

Attesting Officer

Acting Commissioner of Patents and Trademarks